United States Patent [19]

Thomas

[11] Patent Number: 5,109,846
[45] Date of Patent: May 5, 1992

[54] APPARATUS AND METHOD FOR ELECTROTHERAPEUTIC TREATMENT OF STRUCTURES ASSOCIATED WITH THE EYE

[75] Inventor: Gary E. Thomas, Littleton, Colo.
[73] Assignee: PhysioDynamics, Inc., Littleton, Colo.
[21] Appl. No.: 609,480
[22] Filed: Nov. 5, 1990

Related U.S. Application Data

[63] Continuation-in-part of Ser. No. 355,422, May 22, 1989.
[51] Int. Cl.$^5$ ............................................. A61N 1/18
[52] U.S. Cl. ................................... 128/421; 128/793; 128/639; 600/26; 600/27
[58] Field of Search ................... 128/419 R, 421, 792, 128/793, 791, 639, 745; 606/130; 600/26, 27

[56] References Cited

U.S. PATENT DOCUMENTS

| | | | |
|---|---|---|---|
| 793,004 | 6/1905 | May | 128/793 |
| 1,684,860 | 9/1928 | Catlin | 128/793 |
| 3,279,468 | 10/1966 | LeVine | 128/419 R |
| 3,376,870 | 4/1968 | Yamamoto et al. | 128/793 |
| 3,388,699 | 6/1968 | Webb et al. | 128/419 R |
| 4,550,713 | 11/1985 | Hyman | 606/130 |
| 4,902,274 | 2/1990 | Gleeson | 600/27 |

FOREIGN PATENT DOCUMENTS

| | | | |
|---|---|---|---|
| 0325201 | 7/1989 | European Pat. Off. | 128/793 |
| 0641745 | 8/1928 | France | 128/793 |

*Primary Examiner*—William E. Kamm
*Assistant Examiner*—Kennedy J. Schaetzle
*Attorney, Agent, or Firm*—Sheridan Ross & McIntosh

[57] ABSTRACT

The present invention involves a method of treating a patient by providing a signal that is exponential in character to the patient. The signal, includes a relatively low-frequency, constant amplitude, periodic-exponential first component. Further, the signal preferably includes a relatively high-frequency, periodic-exponential second component. The present invention also includes a method and apparatus for non-invasively applying an electrical signal to a structure associated with the eye of the patient. The signal is provided to the structure associated with the eye in the preferred embodiment of the invention by positioning a device for conducting the electrical signal at a point on the exterior of the patient that is substantially interior to the bone structure defining the eye socket. Preferably, the electrical signal is shaped such that an electrical charge is imparted to one or more structures associated with the eye.

17 Claims, 4 Drawing Sheets

APPARATUS AND METHOD FOR ELECTROTHERAPEUTIC TREATMENT OF STRUCTURES ASSOCIATED WITH THE EYE

CROSS-REFERENCE TO RELATED APPLICATION

This is a continuation-in-part of application Ser. No. 07/355,422, filed May 22, 1989 and which is presently pending.

FIELD OF THE INVENTION

The present invention relates to a method and apparatus for treating a patient by providing electrical stimulation to the patient.

BACKGROUND OF THE INVENTION

Among the known types of apparatuses for applying an electrical stimulation to a patient is the interference type apparatus that is used to stimulate structures located within the patient's body, such as muscles and/or the nerves that control muscle action, that are reached with relatively high frequency signals, but are responsive to relatively low frequency signals. The interference apparatus operates by applying two primary signals of relatively high, but slightly different, frequencies to the patient's body. The primary signals, due to their relatively high frequency, penetrate the patient's body and reach the aforementioned structures where they intersect and produce a beat signal having a relatively low frequency that is equal to the slight difference in the frequencies of the primary signals. Exemplary of known interference type apparatuses is U.S. Pat. No. 4,374,524 to Hudek (1983) which illustrates the use of a square-wave signal generator in conjunction with a plurality of phase-locked loops and low-pass filters to produce a plurality of sine-wave, primary signals. Also representative of known interference type apparatuses are U.S. Pat. No. 4,071,033 to Nawracaj et al. (1978), and U.S. Pat. No. 4,153,061 to Nemec (1979) which, in addition to providing two primary signals of different frequencies, also amplitude modulate the primary signals to achieve various therapeutic effects. For example, in Nawracaj two square-wave, primary signals are amplitude modulated by either a square-wave, ramp, exponential, semi-sine or sine-wave signal. In Nemec two sine-wave, primary signals are modulated by two low-frequency sine-wave signals to achieve stimulation at the point of application to the patient's body in addition to producing a beat signal therein.

Another known type of apparatus for applying an electrical stimulation to a patient's body is exemplified in U.S. Pat. No. 4,392,496 to Stenton (1983). Stenton applies two, apparently, square-wave signals to a patient's body in an alternating fashion to achieve muscle stimulation and prevent disuse atrophy. Further, in order to achieve optimal muscle stimulation and enhance the comfort of the patient, Stenton provides for the adjustment of several parameters associated with the applied signals, such as amplitude and frequency.

Yet another apparatus for administering an electrical stimulation to a patient's body is illustrated in U.S. Pat. No. 4,580,570 to Sarrell et al. (1986). The method of Sarrell is characterized by the application of pulses that have a relatively high voltage, high peak but low average current, and short duration. Moreover, the apparatus of Sarrell can be adjusted to apply the aforementioned pulses continuously, periodically, or in an alternating fashion.

Typically, the patient's body produces electrical signals, in the form of sensory and muscle nerve impulses, that are exponential in character. Characteristic, however, of the foregoing apparatuses is the application of signals, like sine-waves and square-waves, that are alien to the typical patient's body. Consequently, the patient can experience a certain amount of discomfort. Moreover, exposure to such alien signals can traumatize certain biological structures associated with the patient. Consequently, there exists a need for a method of electrotherapeutic treatment that produces a signal or signals that more closely resemble the exponential character of the patient's natural signals. There also exists a need for an electrotherapeutic method that produces a signal capable of penetrating the patient's body and that reduces any trauma imposed upon biological structures associated with the patient's body.

Further, others have used electrical stimulation to treat the internal structures of a patient by penetrating a surface that overlies the structure, typically by surgery, and then directly applying the signal to the structure. This is known as an invasive application of an electrical signal to the structure that is to be treated.

Presently, invasive application of electrical signals is being experimentally used in treating the structures associated with the eye that are not directly exposed. These structures include structures interior to the eyeball, such as the vitreous humor and the terminal portion of the optic nerve, as well as structures exterior to the eyeball, such as the muscles that rotate the eyeball. Typically, electrical signals are applied to these structures by surgically exposing the structure, which typically occurs via the roof of the mouth, and then directly applying a signal to the afflicted structure using, for example, needle probes. Typically, this procedure can cause a patient significant amount of pain, inflame the tissues associated with the eye, and/or traumatize certain structures associated with the eye. Moreover, this procedure can facilitate infection of the exposed structures. Further, the procedure is generally impractical for use in correcting afflictions that may require multiple treatments.

Consequently, based on the foregoing, there is also a need for an apparatus and method of non-invasively applying an electrical signal to structures associated with the eye to treat various afflictions or maladies associated the structure. Among the various afflictions or maladies that affect the eye and that application of an electrical signal may be useful in correcting are: presbyopia, muscle imbalance, cataract, glaucoma, inflammation, headache, iritis, anterior ureitis, posterior ureitis, optic nerve neuritis, optic nerve ischemia and visual field defects.

SUMMARY OF THE INVENTION

The present invention involves a method for relieving symptoms associated with injured tissue in a particular region of a patient. The method comprises providing a periodic-exponential signal in that region of the patient.

The present invention also involves a method for decreasing inflammation in an afflicted region in a patient by providing in the region a) a first periodic, double-exponential signal having a frequency between about 0 H and 1000 Hz and b) a second periodic, double-exponential signal having a frequency between about 1000 Hz and 100,000 Hz.

In another embodiment, the present invention involves a method for relieving symptoms associated with injured tissue in a region in a patient. The method comprises a) providing a first periodic-exponential signal; b) providing a second periodic-exponential signal; c) summing the first and second signals to produce a sum signal; and d) applying the sum signal to the region of the patient.

In a further embodiment the present invention involves a method for improving the relative strength of muscles associated with the eyeball. The method comprises providing a periodic-exponential signal to a selected group of the muscles.

In another embodiment, the present invention involves a method for treating an ulcer by providing a periodic exponential signal to the region of the patient containing the ulcer.

Another embodiment of the invention involves treating tissues infected with a virus by providing a periodic-exponential signal to the tissue.

A further embodiment of the instant invention involves blocking plasma kinins from receptor sites in a region in a patient by providing a periodic-exponential signal to the region.

The present invention also provides an apparatus and method for non-invasively applying an electrical signal to a structure associated with a patient's eye. The apparatus includes a device for positioning a conducting device for the electrical signal on an exterior surface of a patient where a substantial portion of the applied electrical signal reaches one or more structures associated with the eye. In the preferred embodiment of the invention, the device for positioning locates the conducting device on the exterior surface of the patient at a location substantially interior to the bone structure defining the patient's eye socket.

In operation, the conducting device is positioned on the exterior surface of the patient at a position that results in a substantial portion of an electrical signal being applied in the region of the eye. Preferably, this involves positioning the conducting device at a point that is substantially within the area defined by the bone structure that forms the frontal aspect eye socket. An appropriate electrical signal is then applied to the eye via the conducting device. The preferred electrical signal is shaped such that an electrical charge is imparted to one or more structures associated with the eye. A signal that has been found to achieve this is the aforementioned periodic exponential signal. Another signal that is believed to be useful in imparting an electrical charge to a structure associated with the eye includes a sinusoidal or alternating component and a dc component.

Based on the foregoing, several advantages of the present invention are apparent. For instance, by non-invasively applying the electrical signal to the structure associated with the eye, the present invention substantially reduces, if not eliminates, the amount of pain, inflammation, and/or trauma associated with invasively applying an electrical signal to the structures associated with the eye. Moreover, the present invention applies an electrical signal to a structure associated with the eye while also substantially avoiding the exposure required in invasive applications of electrical signals that facilitates infection of the structures associated with the eye. Moreover, the present invention facilitates the treatment of afflictions or maladies of structures associated with the eye that require multiple treatments. Currently, the present invention is believed to be useful in treating the following afflictions that affect the eye and associated structures: presbyopia, muscle imbalance, cataract, glaucoma, inflammation, headache, iritis, anterior ureitis, posterior ureitis, optic nerve neuritis, optic nerve ischemia and visual field defects.

DETAILED DESCRIPTION

Figure 1:
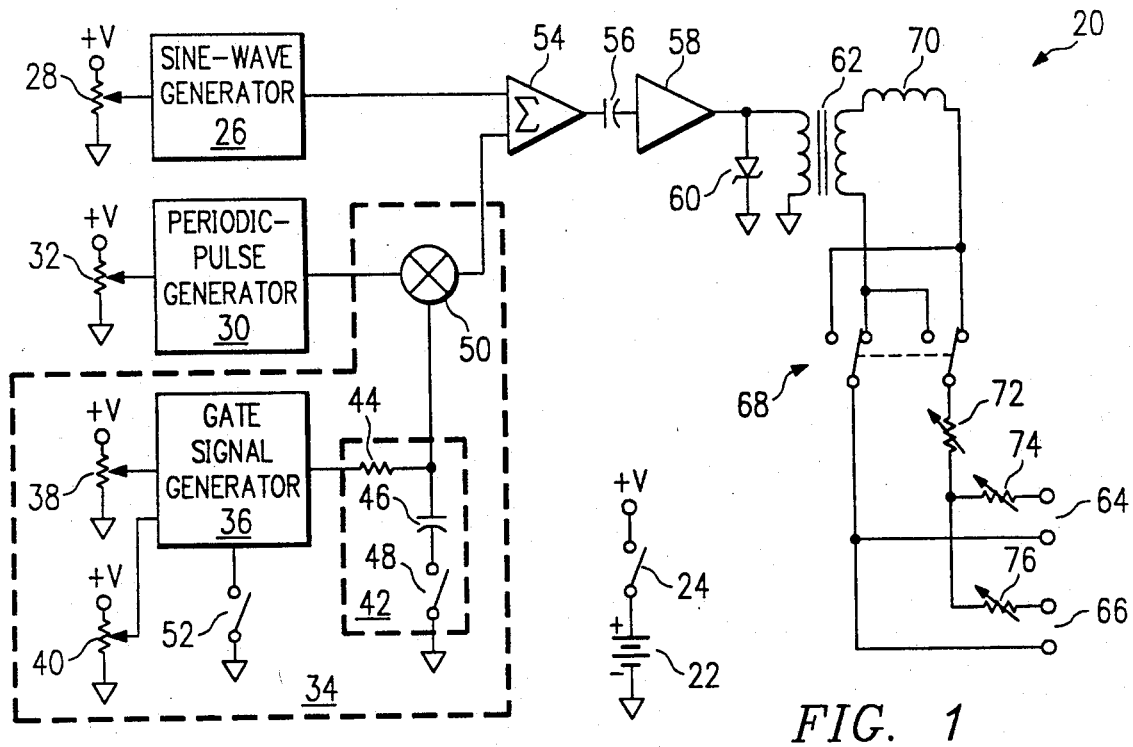
FIG. 1 illustrates a first embodiment of the apparatus useful in the invention.

With reference to FIG. 1, a first embodiment of an apparatus, useful in the practices of the instant method, the electrotherapeutic apparatus 20 (hereinafter referred to as the apparatus 20), is illustrated. The apparatus 20 generates a periodic-exponential signal that is applied to a patient in order to provide the desired treatment. The apparatus also, preferably, generates a periodic-exponential signal that causes sensory stimulation. The term patient as used herein includes vertebrate animals, such as humans, horses, cattle, dogs, cats, birds, snakes and the like.

The apparatus 20 includes a power supply 22, preferably a six-volt battery, for providing operating voltages to the remainder of the apparatus 20. A power supply switch 24 allows an operator to selectively turn "on" and "off" the apparatus 20 by, respectively, connecting and disconnecting the power supply 22 from the remainder of the apparatus 20.

The apparatus 20 further includes a sine-wave generator 26 for producing a constant amplitude sine-wave signal with a frequency of approximately 10-kHz. The 10-kHz sine-wave signal is within the frequency range that is typically used to stimulate the sensory nerves of a patient, i.e., in the range of about 1,000-100,000 Hz. If frequencies outside of this range are found to provide sensory stimulation to the patient, then the frequency of the sine-wave signal produced by the sine-wave generator 26 can be adjusted accordingly. Adjustment of the amplitude of the sine-wave signal is, at least in part, achieved by a first rheostat 28. Preferably, the first rheostat 28 is adjusted when the apparatus 20 is manufactured and is thereafter inaccessible to an operator of the apparatus 20.

The apparatus 20 further includes a periodic-pulse generator 30 for producing a constant amplitude periodic-pulse signal with a frequency ranging from 40 Hz to 500 Hz. The frequency of the periodic-pulse signal encompasses the frequency spectrum that is generally used to stimulate the muscles of a patient, i.e. D.C. to 1,000 Hz. If frequencies outside of this range are found to provide muscle stimulation to the patient, then the frequency of the periodic-pulse signal produced by the periodic-pulse generator 30 can be adjusted accordingly. Adjustment of the frequency of the periodic-pulse signal is provided by a second rheostat 32.

Also included in the apparatus 20 is a gating means 34 for selectively gating the periodic-pulse signal produced by the periodic-pulse generator 30 in a periodic fashion. In other words, the gating means 34 operates to alternatingly allow and inhibit the passage of the stimulation periodic-pulse signal to the patient's body. The preferred gating means 34 includes a gating signal generator 36 for producing a periodic-pulse signal, hereinafter referred to as the gating signal. The period of the gating signal can be adjusted from approximately five seconds to one minute by a third rheostat 38. A fourth rheostat 40 allows the duty cycle of the gating signal to be adjusted from about five percent to about ninety-five percent. Further included in the preferred gating means 34 is a gradual on-off means 42 for selectively smoothing the rising and falling edges of the gating signal thereby producing the effect of gradually allowing and inhibiting the passage of the stimulation signal. The preferred gradual on/off means 42 includes a resistor 44 and a capacitor 46 which, when a first switch 48 is closed, act as a low-pass filter that smoothes the rising and falling edges of the gating signal. The preferred gating means 34 further includes a multiplier 50 for alternatingly allowing and inhibiting the passage of the periodic-pulse signal output by the periodic-pulse generator 30 according to the gating signal. For example, if the gating signal is zero then the multiplier 50 inhibits the passage of the periodic-pulse signal. If, on the other hand, the gating signal is non-zero, then the multiplier 50 allows the periodic-pulse signal or a portion thereof to pass. Additionally, the preferred gating means 34 includes a second switch 52 for allowing an operator to selectively allow or inhibit the gating signal from reaching the multiplier 50. In other words, the second switch 52 gives the operator the option of using or not using the gating apparatus 34. Specifically, when the second switch 52 is open, the gating signal is applied to the multiplier 50 and the periodic-pulse signal is gated accordingly. When the second switch 52 is closed, the gating signal is not applied to the multiplier 50 and the multiplier 50 allows the periodic-pulse signal to pass unattenuated. The apparatus 20 further includes a summing amplifier 54 for adding the sine-wave signal produced by the sine-wave generator 26 and the periodic-pulse signal output by the multiplier 50 to produce a sum signal. One cycle of the sum signal, less any DC component, includes a first portion and a second portion. The first portion reflects the sum of the sine-wave signal and the pulse portion of the periodic-pulse signal. The second portion reflects the sum of the sine-wave signal and the portion of the periodic-pulse signal when the pulse is absent. Since the periodic-pulse signal is zero when the pulse is absent, the second portion of the sum signal is, essentially, just the sine-wave signal.

Apparatus 20 further includes an AC coupling capacitor 56 and, a power amplifier 58 and a zener diode 60. The AC coupling capacitor 56 serves, at least in part, to eliminate any DC component in the sum signal output by the summing amplifier 54. The AC coupling capacitor 56 can be either a discrete component or the capacitance associated with the power amplifier 58 can be used. Similarly, the zener diode 60 can be either a discrete component or the breakdown characteristics of the power amplifier 58 can be employed. Preferably, the AC coupling capacitor 56 and the zener diode 60 are realized by using the capacitance and breakdown characteristics of the power amplifier 58, respectively. Consequently, the AC coupling capacitor 56 and zener diode 60 shown in FIG. 1 are representations of the capacitance and breakdown characteristics of the power amplifier 58. The operation of the capacitor 56, power amplifier 58 and zener diode 60 is now described during the first and second portions of a single cycle of the sum signal output by the summing amplifier 54. The first portion of the sum signal passes through the capacitor 56 to the power amplifier 58 where it drives the power amplifier 58 into the cutoff region. When the power amplifier 58 is in the cutoff region it does not output any current. The zener diode 60, however, cooperates with a transformer to maintain a defined voltage at the output of the power amplifier 58 for the duration of the first portion of the sum signal. Further, the zener diode 60 operates to blank out a substantial portion of the sine-wave signal aspect of the first portion of the sum signal. Consequently, a pulse having the defined current is produced at the output of the power amplifier 58 even though the power amplifier is operating in the cutoff region. In addition, while the power amplifier 58 is in cutoff, the bias voltage supplied by the power supply 22 charges the capacitor 56. The second portion of the sum signal is substantially unaffected by the operation of the zener diode 60. The capacitor 56 and the power amplifier 58 do, however, affect the second portion of the sum signal. Specifically, the capacitor 56 passes the second portion of the sum signal on to the power amplifier 58 and discharges the charge accumulated during the first portion of the sum signal into the power amplifier 58 in an exponential fashion. The discharging of the capacitor 56 results in the second portion of the sum signal being exponentially amplitude modulated. Once the capacitor 56 is completely discharged, exponential amplitude modulation of the second portion of the sum signal ceases and a constant amplitude steady state is attained. The second portion of the sum signal also drives the power amplifier into saturation during a portion of each cycle of the sine-wave signal that comprises the second portion of the sum signal. Consequently, the power amplifier 58 also clips a portion of each cycle of the sine-wave signal. In summary, the one cycle of the sum signal produced at the output of the power amplifier 58 includes a pulse, the first portion, and a clipped sine-wave signal that is, for a time, exponentially amplitude modulated the second portion.

The apparatus 20 also preferably includes a step-up transformer for increasing the voltage of the sum signal existing at the output of the power amplifier 58. In the preferred embodiment the step-up transformer is a 1:10 step-up transformer 62. The sum signal at the output of the step-up transformer 62 is, following further processing discussed hereinafter, distributed to means for applying it to the patient. In the embodiment illustrated in FIG. 1, the sum signal output by the step-up transformer 62 is, int he preferred embodiment, distributed to a first pair of pads 64 and a second pair of pads 66 that are applied to the patient's skin. Alternatively, the sum signal can be distributed to applicators, such as point applicators, that can be moved over the patient's skin during treatment. Other means for applying the sum signal to the patient include an internal applicator that is inserted into the body of the patient, such as a needle electrode, and a remote applicator, such as a transmission antenna.

A double-pole, double-throw switch 68 allows an operator to change the polarity of the sum signal applied to the first and second pairs of pads 64,66.

The apparatus 20 further includes a shaping means that is used to exponentially shape the sum signal output the transformer 62 and applied to the patient by the first pair of pads 64 and/or the second pair of pads 66. With reference to a single cycle of the sum signal, exponential shaping results int he rising and/or falling aspects of the first portion of the sum signal including an exponential component. Exponential shaping also, preferably, results int he rising and/or falling aspects of each cycle of the sine-wave signal comprising the second portion of the sum signal including an exponential component. Preferably, the shaping means is used to impart a double-exponential character to the sum signal where both the rising and falling edges of the first portion of the sum signal and each cycle of the sine-wave signal in the second portion of the sum signal include an exponential component. Preferably, the shaping means includes an inductor-resistor network comprising an inductor 70, a fifth rheostat 72, a sixth rheostat 74 and a seventh rheostat 76. The inductor 70 can be either a discrete component or incorporated into the transformer 62. The inductor 70, the fifth rheostat 72, sixth rheostat 74, seventh rheostat 76 and the electrical load provided by the patient cooperate to exponentially shape the sum signal existing at the first pair of pads 64. While not wishing to be bound by theory, it is believed that the following explanation correctly models the interaction of the shaping means and the patient in exponentially shaping the sum signal produced at the first pair of pads 64. The inductor 70, fifth rheostat 72 and sixth rheostat 74 define, at least in part, the "L/R" exponential time constant that determines the exponential character of the sum signal applied to the patient by the first pair of pads 64. The electrical load provided by the patient also defines, at least in part, the "L/R" exponential time constant that determines the exponential character of the sum signal applied to the patient by the first pair of pads 64. Specifically, the inductor 70 defines the "L" portion of the exponential time constant and the fifth rheostat, sixth rheostat and resistance provided by the patient across the first pair of pads 64 determines the "R" portion of the exponential time constant. The resistance across the first pair of pads 64 is substantially infinite when they are not attached to a patient. Consequently, the exponential time constant approaches zero and the sum signal output by the transformer 62 is substantially unaffected. If, however, the first pair of pads 64 are attached to a patient, then a non-zero exponential time constant is established and the sum signal is shaped accordingly. Specifically, the patient establishes a finite resistance across the first pair of pads 64 which, in combination with inductor 70, fifth rheostat 72 and sixth rheostat 74, defines a non-zero exponential time constant. Consequently, the exponential character of the sum signal applied to the patient is defined in part by the resistance provided by the patient, i.e., the sum signal accommodates to the patient. The patient is roughly modeled as a resistance in series with a large capacitor. The "RC" exponential time constant associated with the patient is relatively large with respect to the aforementioned "L/R" time constant. Consequently, the capacitance associated with the patient is relatively insignificant and can be ignored for purposes of explaining the interaction between the patient and the shaping means. Adjustment of the fifth rheostat 72 and/or the sixth rheostat 74 alters the exponential time constant and, hence, the exponential character of the sum signal applied to the patient by the first pair of pads 64. In addition, adjustment of the fifth rheostat 72 and/or the sixth rheostat 74 affects the amplitude of the sum signal applied to the patient by the first pair of pads 64. The inductor 70, fifth rheostat 72 and seventh rheostat 76 operate in an identical fashion with respect tot he sum signal applied to the patient by the second pair of pads 66. A shaping means that does not interact with the electrical load provided by the patient is also feasible.

Figure 2A:
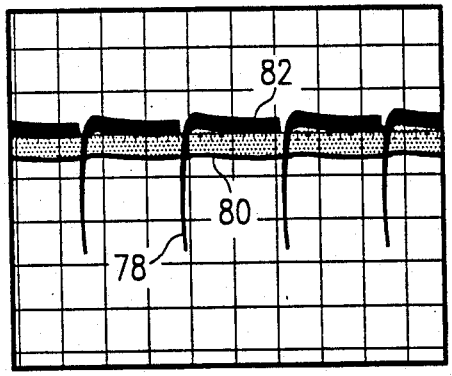
FIG. 2A illustrates several cycles of the sum signal that is applied to a patient's body by the apparatus shown in FIG. 1.
Figure 2B:
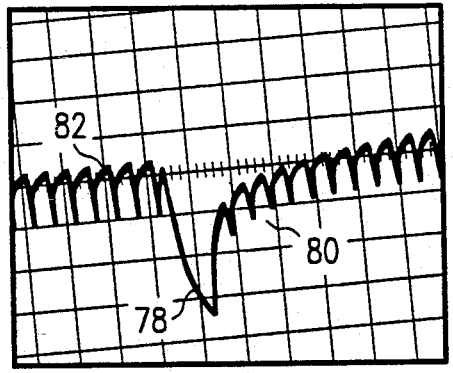
FIG. 2B illustrates a portion of a single cycle of the sum signal that is applied to a patient's body by the apparatus in FIG. 1.
Figure 2C:
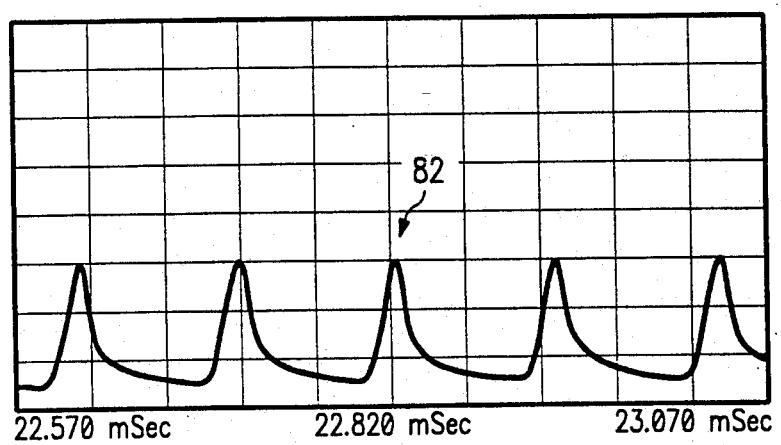
FIG. 2C illustrates the substantially constant amplitude periodic-exponential portion of the sum signal that is applied to a patient's body by the apparatus shown in FIG. 1.

FIGS. 2A and 2B illustrate the sum signal applied to the patient by either the first pair of pads 64 or the second pair of pads 66 with the double-pole, double-switch 68 in a first orientation. The sum signal includes a substantially constant amplitude, periodic-exponential portion 78 suitable for muscle stimulation. The sum signal also includes an exponentially amplitude modulated, clipped, periodic-exponential portion 80. As shown in FIGS. 2A–2C, the exponential amplitude modulation eventually terminates and a clipped, periodic-exponential signal 82 results. The clipped, periodic-exponential signal 82 shown in FIG. 2C was produced with the double-pole, double-throw switch 68 in a second orientation. Consequently, the clipped, periodic exponential signal 82 in FIG. 2C is the mirror image or opposite polarity of the corresponding clipped, periodic-exponential signals shown in FIGS. 2A and 2B.

Figure 3:
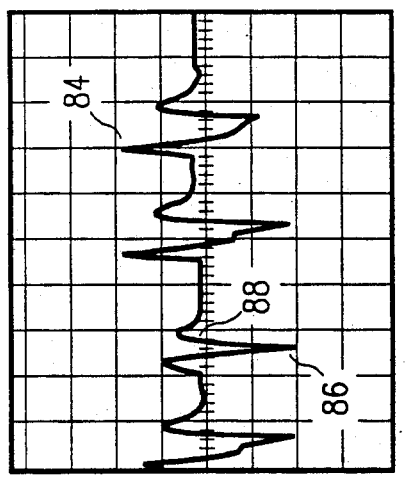
FIG. 3 shows the signal naturally produced by a human patient.

FIG. 3 shows a natural signal 84 produced by a human patient. The natural signal 84 includes a double-exponential portion 86 that corresponds to the constant amplitude, periodic-exponential signal 78 produced by the apparatus 20. The natural signal 84 also includes an exponentially amplitude modulated portion 88 that corresponds to the exponentially amplitude modulated, clipped, periodic-exponential signal produced by the apparatus 20. Consequently, the sum signal produced by the apparatus 20 corresponds, at least in part, to the signal 84 naturally produced by the human patient.

Operation of the apparatus 20 includes an initialization phase where the power supply switch 24 is placed in the "off" position to insure that when the pads are subsequently applied to the patient an undesirable signal is not also applied to the patient. Initialization also involves setting the fifth, sixth and seventh rheostats 72, 74, 76 for maximum attenuation to insure that the minimum amplitude sum signal is applied to the patient when the power supply switch 24 is closed. Further, the second rheostat 32 is set such that the periodic-pulse generator 30 will produce a periodic-pulse signal having a frequency at or about the mid-range of possible frequencies when the power supply switch 24 is closed. Also during initialization, the third and fourth rheostats 38, 40, are set such that when the power supply switch 24 is closed, a gating signal will be produced by the gate signal generator 36 that has a frequency in the mid-range of possible frequencies and a duty cycle of about fifty percent. During initialization, the second switch 52 is opened to insure that the gating signal is applied to the multiplier 50 when the power supply switch 24 is closed. Additionally, the first switch 48 is closed during initialization so that when the power supply switch 24 is closed the gating signal produced by the gate signal generator 36 is smoothed before application to the multiplier 50. Following initialization of the aforementioned switches and rheostats, the first pair of pads 64 and/or the second pair of pads 66 are attached to the patient's body at the points where muscle stimulation is desired. Preferably, treatment is effected along the longitudinal axis of the muscle. Preferably a pad is placed at each end of the muscle along the longitudinal axis of the muscle with the muscle itself between the pads with one pad preferably placed closer to the center of the body of the patient. If the muscle being treated is a frontal muscle, then the pad should be placed on the frontal part of the body. If a dorsal or posterior muscle is involved, then the pads should be placed on the dorsal part of the body. If it is not possible to treat the muscle along its longitudinal axis, then transverse treatment of the muscle can be effective. In this case, the pads are placed perpendicular to the longitudinal axis of the muscle being treated. Once the pads are attached to the patient, the power supply switch 24 is closed and the apparatus 20 generates the sum signal comprising the substantially constant amplitude, periodic-exponential signal 78 and the exponentially amplitude modulated, clipped, periodic-exponential signal 80. The sum signal is applied to the patient via the pads. Due to the aforementioned adjustment of the fifth, sixth and seventh rheostats 72, 74, 76 the sum signal applied to the patient is of minimum amplitude. At this point the exponential character and amplitude of the sum signal being applied to the patient can be adjusted using the fifth rheostat 72 and the sixth or seventh rheostats 74, 76. In addition, the frequency of the periodic-pulse portion of the sum signal can be adjusted using the second rheostat 32. Adjustment of the frequency and duty cycle of the gating signal can be accomplished by manipulating the third and fourth rheostats 38, 40. If the gating signal is not desired, then the second switch 52 can be closed.

Figure 4:
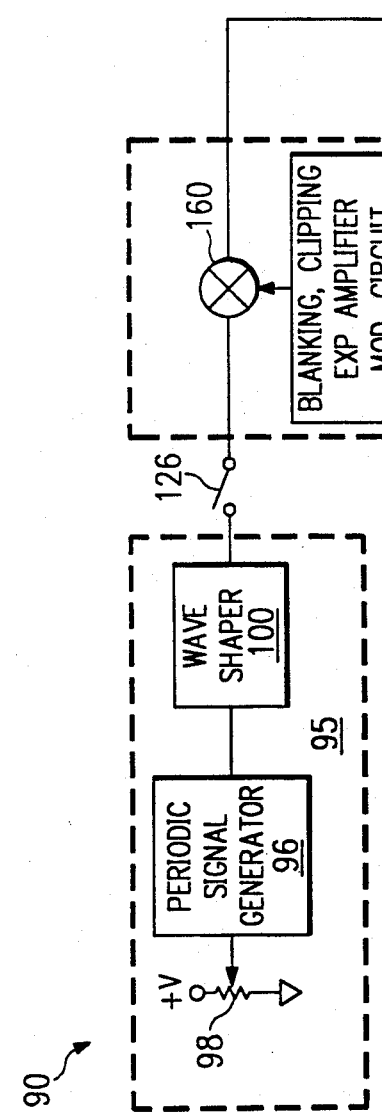
FIG. 4 illustrates a second apparatus useful in the invention.
Figure 4:
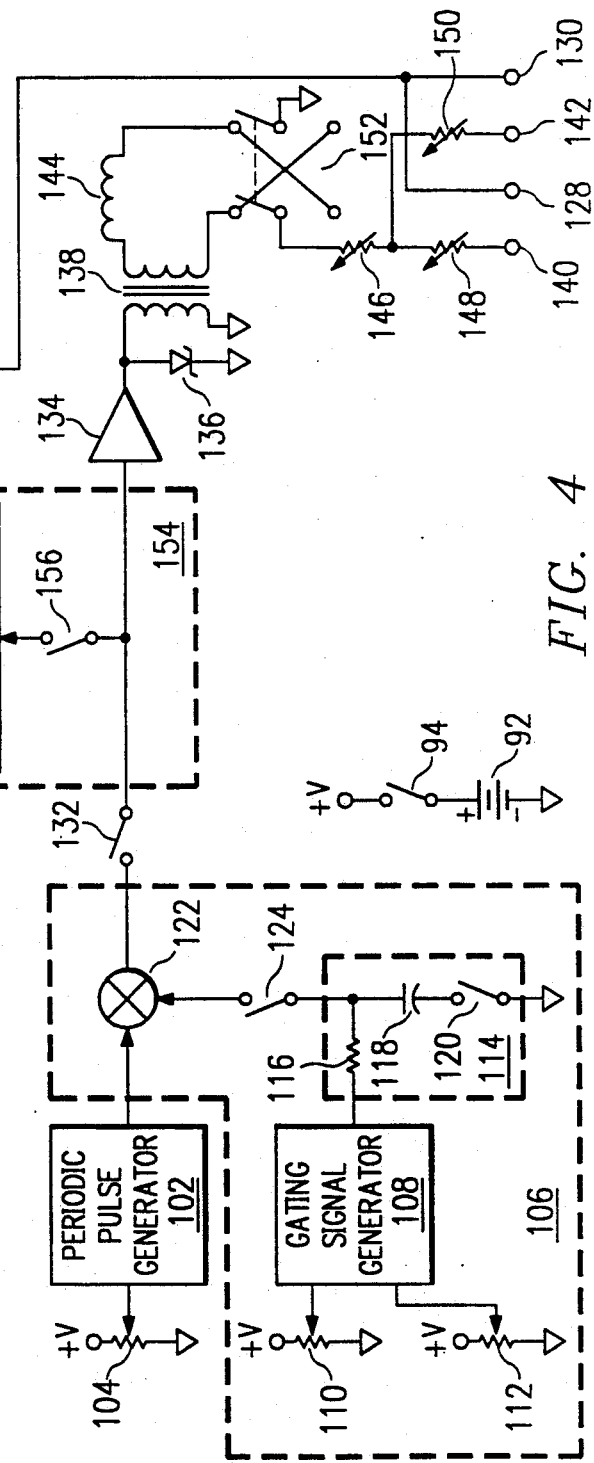

FIG. 4 illustrates a second embodiment of the invention, i.e., the electrotherapeutic apparatus 90 (hereinafter referred to as the apparatus 90). Apparatus 90, in contrast to apparatus 20, does no sum a sine-wave signal and a periodic-pulse signal. Rather, apparatus 90 applies the a periodic-exponential signal suitable for sensory stimulation and a periodic-exponential pulse signal suitable for muscle stimulation to the body of the patient over separate paths. The apparatus 90 allows an operator to control whether the periodic-exponential signal suitable for sensory stimulation, periodic-exponential pulse signal suitable for muscle stimulation or both signals are applied to the patient. The apparatus 90 also allows the operator to selectively blank, exponentially amplitude modulate, and clip the periodic-exponential signal used for sensory stimulation.

The apparatus 90 includes a power supply 92 and power supply switch 94 which operate in a substantially similar fashion to the power supply 22 and the power supply switch 24 of apparatus 20.

The apparatus 90 further includes a periodic-exponential signal generator 95 for producing a constant amplitude periodic-exponential signal having a frequency appropriate for stimulation of the sensory nerves of a patient. The preferred periodic-exponential signal generator 95 includes a periodic signal generator 96 for outputting a constant amplitude periodic signal. Preferably, the power associated with the periodic signal output by the periodic signal generator 96 is sufficient to penetrate the patient's body. Amplitude adjustment of the periodic signal output by the periodic signal generator 96 is provided by a first rheostat 98. Preferably, the first rheostat 98 is adjusted when the apparatus 90 is manufactured and is thereafter inaccessible. The periodic signal output by the periodic signal generator 96 can have virtually any shape since the preferred periodic-exponential generator 95 includes a wave-shaper 100 that is designed to modify the shape of whatever signal is being output by the periodic signal generator 96 to produce a constant amplitude periodic-exponential signal. For example, if the periodic signal generator 96 is outputting a constant amplitude square-wave signal, then the wave-shaper is designed to modify the square-wave shape to a periodic-exponential shape. Exponential shaping of the periodic signal output by the periodic signal generator results int he rising and/or falling aspects of the periodic signal having an exponential component. Preferably, the wave-shaper 100 imparts a double-exponential character to the periodic signal where both the rising and falling aspects have an exponential component.

The apparatus 90 further includes a periodic-pulse signal generator 102 for generating a periodic-pulse signal having a frequency suitable for muscle or motor stimulation of a patient. The frequency of the stimulation pulse signal output by the stimulation periodic pulse signal generator 102 is adjusted by manipulating a second rheostat 104.

The apparatus 90 further includes a gating means 106 that alternatingly allows and inhibits the passage of the periodic-pulse signal. The preferred gating means 106 includes a gating signal generator 108 for producing a gating signal. The period and duty cycle of the gating signal produced by the gating signal generator 108 can be adjusted by, respectively, a third rheostat 110 and a fourth rheostat 112. A gradual on/off means 114, preferably comprising a resistor 116, a capacitor 118 and a first switch 120, provides an operator with the option of smoothing the rising and falling edges of the gate signal such that the periodic-pulse signal is gradually applied and then removed from the patient. A first multiplier 122 gates the periodic-pulse signal produced by the periodic-pulse signal generator 102 according to the gating signal. A second switch 124 provides an operator with the option of using or not using the gating apparatus 106.

The apparatus 90 further includes a third switch 126 that gives an operator with the option of providing or not providing the background periodic-exponential signal output by the waive-shaper 100 to a means for applying the signal to the patient. Specifically, if the third switch 126 is open then the periodic-exponential signal is not applied to the patient. When the third switch 126 is closed, the periodic-exponential signal is applied to the patient using one or more pads attached to the patient's skin. Preferably, a first pad 128 and a second paid 130 are employed to apply the periodic-exponential signal to the patient. Alternatively, the periodic-exponential can be applied to the patient's skin using a point applicator that can be moved over the patient's skin during treatment. Other means for applying the periodic-exponential signal to the patient include an internal applicator, such as a needle electrode inserted into the body of the patient, and a remote applicator, like a transmission antenna.

The apparatus 90 further includes a fourth switch 132 for providing an operator with the option of applying or not applying the periodic-pulse signal to the patient. Specifically, when the fourth switch 132 is open, the stimulation periodic-pulse signal is not applied to the patient. However, when the fourth switch 132 is closed, the periodic-pulse signal output by the first multiplier 122 is applied to a power amplifier 134 which amplifies the periodic-pulse signal. The amplified periodic-pulse signal is then applied to a regulator, which in the preferred embodiment is a zener diode 136. The zener diode 136 can be a discrete component or the breakdown characteristic of the power amplifier 134 can be employed. Once processed by the zener diode 136, the periodic-pulse signal is applied to a step-up transformer for increasing the voltage of the periodic-pulse signal. In the preferred embodiment of apparatus 90, a 1:10 step-up transformer 138 is used.

The periodic-pulse signal output by the transformer 138 is, following processing described more thoroughly hereinafter, distributed to means for applying it to the patient. In the embodiment illustrated in FIG. 4, the periodic-pulse signal is applied to a patient using one or more pads attached to the patient's skin. Preferably, a third pad 140 and a fourth pad 142 are used to apply the periodic-pulse signal to the patient. Alternatively, the periodic-pulse signal can be applied to the patient's skin using a point applicator that can be moved over the patient's skin during treatment. Other means for applying the periodic-pulse signal to the patient include a device inserted into the interior of the patient's body, like a needle electrode, and a remote applicator, like a transmission antenna.

The apparatus 90 further includes a shaping means that is used to exponentially shape the periodic-pulse signal output by the transformer 138 and applied to the patient by the third and fourth pads 140, 142. Exponential shaping of the periodic-pulse signal results in the rising and/or falling aspects of the pulse in the periodic-pulse signal include an exponential component. Preferably, the shaping means imparts a double-exponential character to the periodic-pulse signal where both the rising and falling of the pulse in each cycle of the periodic-pulse signal include an exponential component. Preferably, the shaping means includes an inductor-resistor network comprising an inductor 144, a fifth rheostat 146, a sixth rheostat 148, and a seventh rheostat 150. The inductor 144 can be either a discrete component or incorporated into the transformer 138. The inductor-resistor network operates, as previously discussed with respect to apparatus 20, to modify the periodic-pulse signal output by the transformer 138 such that the periodic-pulse signals applied to the patient by the third and fourth pads 140, 142, are constant amplitude periodic-exponential signals.

A double-pole, double throw switch 152 allows an operator to change the polarity of the constant amplitude periodic-exponential signals applied to the patient by the third and further pads 140, 142.

The apparatus 90 also includes a blanking, clipping and exponentially amplitude modulating circuit 154 for blanking the periodic-exponential signal output by the wave shaper 100 when a pulse associated with the periodic-exponential signal output by the multiplier 122 is present and clipping, together with exponentially amplitude modulating, the periodic-exponential signal otherwise. The blanking, clipping and exponentially amplitude modulating circuit 154 is comprised of a fifth switch 156, a blanking, clipping and exponential amplitude modulating signal generator 158 and a second multiplier 160. The blanking, clipping and exponential amplitude modulating circuit 154 operates such that when the fifth switch 156 is closed, the blanking, clipping and exponentially amplitude modulating signal generator 158 produces a signal that, upon application to the second multiplier 160, results in the periodic-exponential signal being blanked during the presence of a pulse associated with the periodic-exponential pulse signal and clipped, together with exponentially amplitude modulated, otherwise.

With reference to FIGS. 2A–2C, the various signals that can be applied to the patient by manipulation of the third switch 126 and the fourth switch 132 are illustrated. When the third switch 126 is closed and the fourth switch 132 is open, a constant amplitude, periodic-exponential signal 82 having a frequency suitable for sensory stimulation is applied to the patient. When the third switch 126 is open and the fourth switch 132 is closed, a constant amplitude periodic-exponential signal 78 having a frequency suitable for muscle stimulation is applied to the patient. When both the third switch 126 and the fourth switch 132 are closed, both of the constant amplitude periodic-exponential signal 78 and the periodic-exponential signal 82 are applied to the patient. Further, if both the third switch 126 and the fourth switch 132 are closed, then the fifth switch can be closed to blank, clip and exponentially amplitude modulate the periodic-exponential signal 82. Once the appropriate signal or signals have been selected then the operator can manipulate the rheostats to further modify the signal or signals being applied to the patient.

Operation of the apparatus 90 includes an initialization phase where the power supply switch 94 is placed in the "off" position to insure that when the pads are subsequently applied to the patient an undesirable signal is not also applied to the patient. Initialization also involved setting the fifth, sixth and seventh rheostats 146, 148, 150 for maximum attenuation to insure that the minimum amplitude periodic-exponential signal, if selected, is applied to the patient upon the closing of the power supply switch 94. Further, the second rheostat 104 is set such that the periodic-pulse generator 102 produces a periodic-pulse signal having a frequency at or about the mid-range of possible frequencies. Also during initialization the third and fourth rheostats 110, 112, are set such that upon the closing of the power supply switch 94 a gating signal is produced by the gate signal generator 108 that has a frequency in the mid-range of possible frequencies an a duty cycle of fifty percent. During initialization, the second switch 124 is closed to insure that the gating signal is applied to the multiplier 122 when the power supply switch 94 is closed. Additionally, the first switch 120 is closed during initialization so that when the power supply switch 94 is closed the gating signal produced by the gate signal generator 108 is smoothed before application to the multiplier 50. Also during initialization of the third switch 126, fourth switch 132 and fifth switch 156 are opened or closed depending upon what type of signal is desired. Following initialization of the aforementioned switches and rheostats, one or more of the pads are attached to the patient's body at the points where muscle stimulation is desired. Preferably, treatment is effected along the longitudinal axis of the muscle. Preferably a pad is placed at each end of the muscle along the longitudinal axis of the muscle with the muscle itself between the pads with one pad preferably placed closer to the center of the body of the patient. If the muscle being treated is a frontal muscle, then the pad should be placed on the frontal part of the body. If a dorsal or posterior muscle is involved, then the pads should be place don the dorsal part of the body. IF it is not possible to treat the muscle along its longitudinal axis, then transverse treatment of the muscle can be effective. In this case, the pads are placed perpendicular to the longitudinal axis of the muscle being treated. Once the pads are attached to the patient, the power supply switch 94 is closed and the desired signal is generated by the apparatus 90 and applied to the patient via the pads. Due to the aforementioned adjustment of the fifth, sixth, and seventh rheostats 146, 148, 150 the periodic-pulse signal, if applied to the patient, is of a minimum amplitude. If the periodic-exponential pulse signal is applied to the patient, its amplitude can be adjusted using the fifth, sixth and seventh rheostats 146, 148, 150. In addition, the frequency of the periodic-exponential pulse can be adjusted using the second rheostat 104. Further, if the gating signal is being used, its frequency and duty cycle can be adjusted by manipulating the third and fourth rheostats 110, 112. If the gating signal is not desired, then the second switch 124 can be opened.

Figure 5:
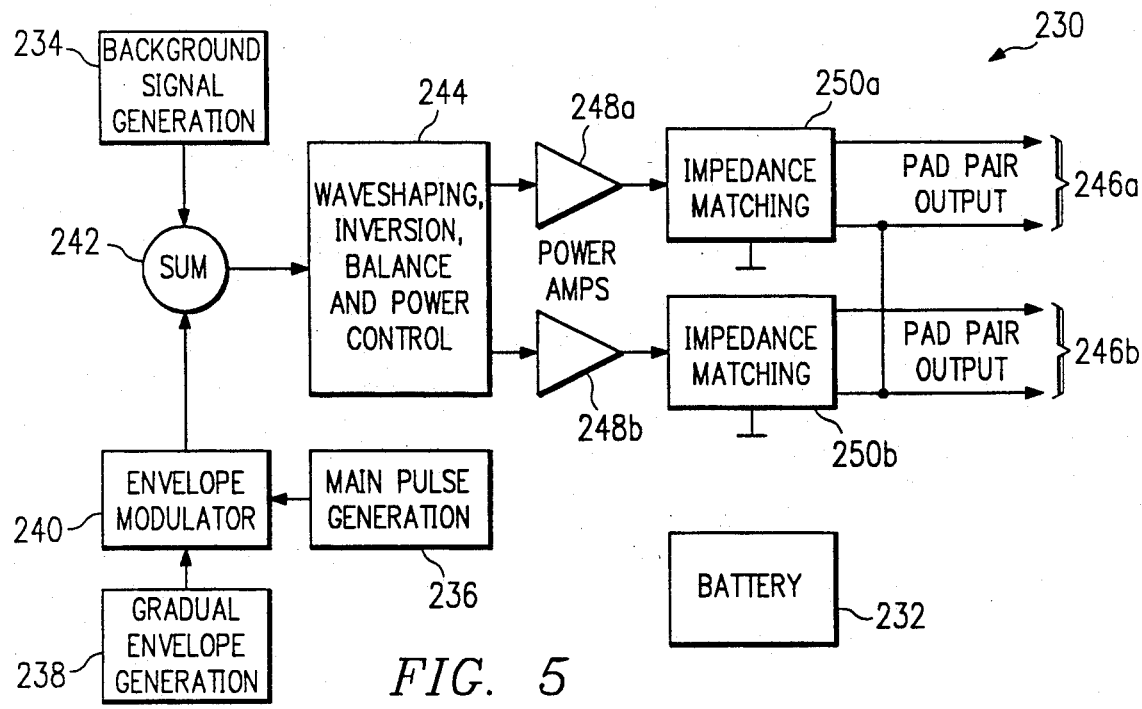
FIG. 5 illustrates another embodiment of the apparatus useful in practicing the invention.
Figure 6D:
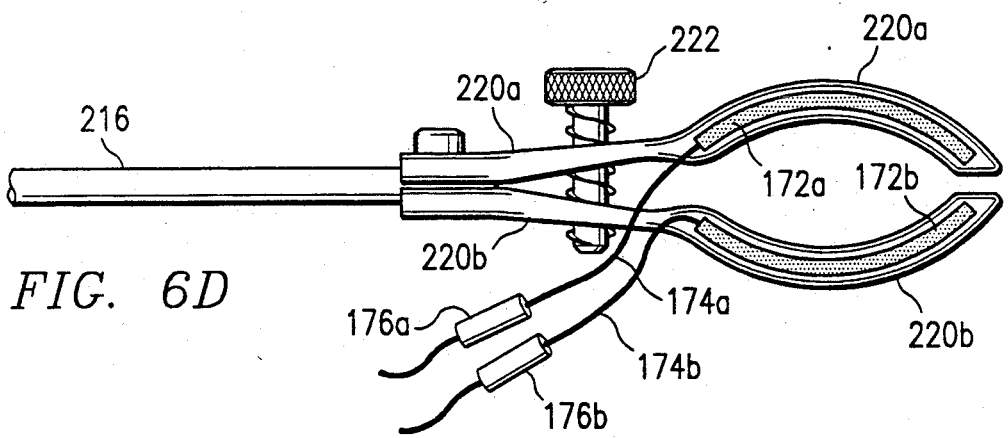
FIG. 6D is a detailed view of the electrodes and a portion of the electrode positioning member illustrated in FIG. 6A.
Figure 8:
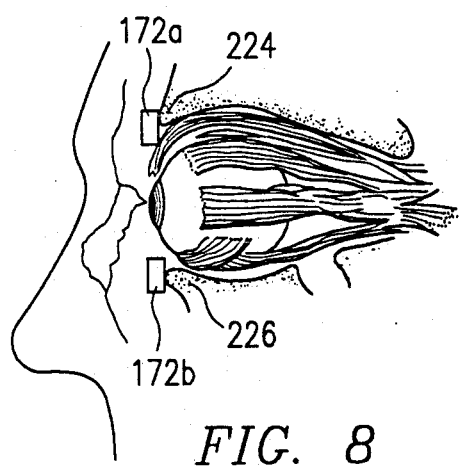
FIG. 8 is a cutaway side view that illustrates the positional relationship of the conducting pads to the bone structure that defines the frontal aspect of a patient's eye socket.
Figure 7:
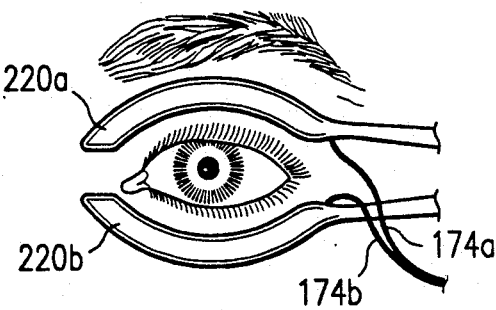
FIG. 7 is a frontal illustration of the relationship between the electrode positioning member and a patient's eye.
Figure 6B:
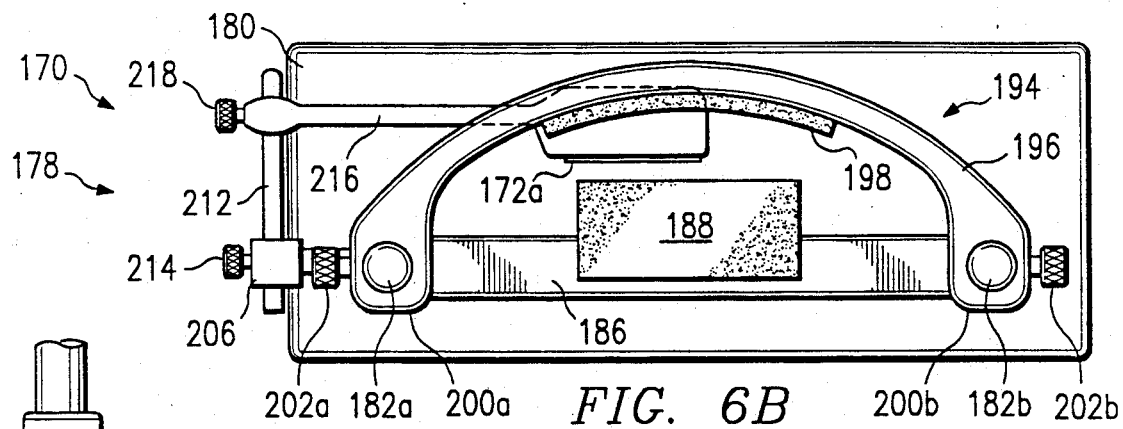
FIG. 6B is a top view of the apparatus shown in FIG. 6A.
Figure 6C:
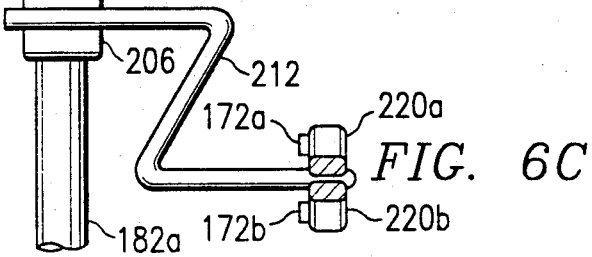
FIG. 6C is a side view of the electrode positioning member of the apparatus illustrated in FIG. 6A.
Figure 6A:
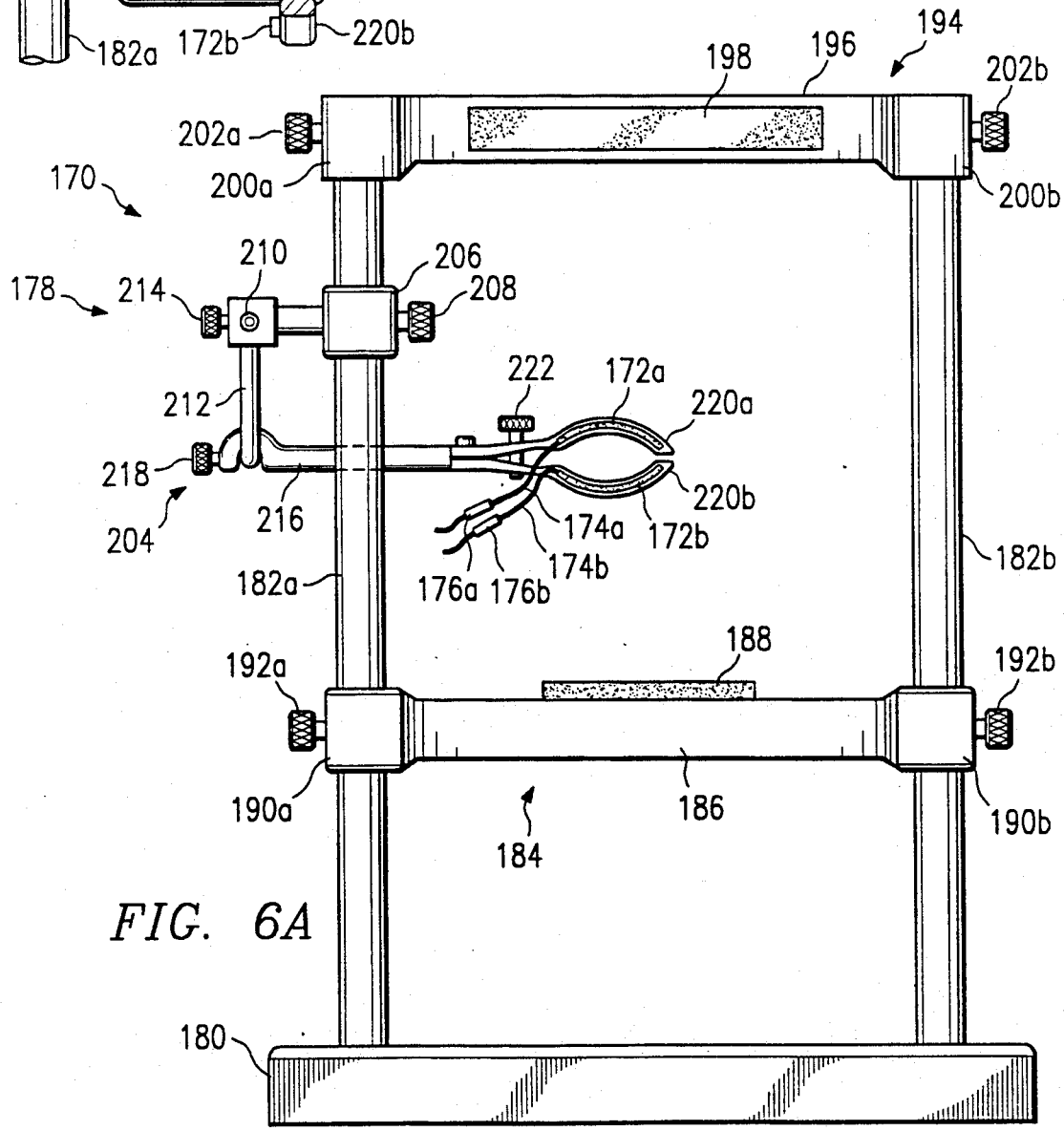
FIG. 6A is a frontal view of the preferred embodiment of an apparatus for use in applying an electrical signal to structures associated with a patient's eye.

With reference to FIG. 5, another embodiment of apparatus for generating a periodic-exponential signal 230, hereinafter referred to as apparatus 230, is illustrated. The apparatus 230 includes a battery 232 for selectively providing power to the remainder of apparatus 230. The apparatus 230 also includes a background signal generator 234 for producing a substantially constant peak amplitude sine-wave signal having a frequency of approximately 10-kHz. Also included in the apparatus 230 is a main pulse generator 236 for producing a substantially constant peak amplitude periodic-pulse signal having a frequency ranging from approximately 40 Hz to 500 Hz. The frequency, amplitude, and duty cycle of the periodic-pulse produced by the main pulse generator 236 can be adjusted using rheostats (not shown). The apparatus further includes a gradual envelope generator 238 that is applied to an envelope modulator 240 to "smooth" the periodic-pulse signal produced by the main pulse generator 236, which is also applied to the envelope modulator 240, by exponentially modulating the periodic-pulse signal. The gradual envelope generator 238 functions in much the same manner as the gradual on-off means shown in FIG. 1. A summer 242 is employed to sum the sine-wave signal produced by the the background signal generator 234 with the "smoothed" periodic-pulse signal output by the envelope modulator 240. The output of the summer 242 is applied to a waveshaping, inversion, balance, and power control circuit 244, hereinafter referred to as circuit 244. The circuit 244 provides the waveshaping, which may include inversion, necessary to achieve a signal substantially like that shown in FIGS. 2A-C and FIG. 3. The circuit 244 also includes rheostats (not shown) for adjusting the balance and the power of the signal output by the circuit 244. The rheostats associated with the circuit 244 achieve substantially the same effect as the fifth rheostat 72, sixth rheostat 74, and seventh rheostat 76 shown in FIG. 1. The circuit 244 outputs two of the appropriately shaped signals, one for each of a pair of pads 246a, 246b. However, before the signals are applied to the pads 246a, 246b, the signals are amplified by power amplifiers 248a, 248b, and applied to impedance matching circuits 250a, 250b. The power amplifiers 248a, 248b, increase the power of the signals output by the circuit 244. The impedance matching circuits 250a, 250b, reduce any impedance mismatch between the circuitry preceding the impedance matching circuits 250a, 250b, and the impedance of the patient as it exists across the pads 246a, 246b. By reducing any impedance mismatch, more of the signals produced by the circuit 244 are applied to the patient. Preferably, the impedance matching circuits 250a, 250b, include appropriately would transformers.

The operation of the apparatus 230 is substantially similar to that described with respect to the embodiments illustrated in FIGS. 1 and 4. Specifically, the battery 232 is placed in the "off" condition so that no power is being applied to the remainder of the apparatus 230 and the rheostats associated with the main pulse generator 236 and circuit 244 are adjusted so that the minimum signal will be produced at the pads 246a, 246b, when the apparatus 230 is turned on. One or both pairs of the pads 246a, 246b, are then applied at the appropriate locations on the patient and the battery 232 is switched "on" to apply power to the remainder of the apparatus 230. The rheostats associated with the main pulse generator 236 and circuit 244 are then adjusted to produce the appropriate signal for treating the patient's affliction.

Application of the above-described periodic-exponential signal is particulary useful in the treatment of a number of afflictions of vertebrate animals. Generally in conducting the treatment, it is preferred to apply the signal at a power setting which is past the point of complete comfort to the patient but below the threshold of pain. The application of such a signal is useful in treating or relieving certain symptoms associated with injured tissue in a patient. The present process is also useful in treating certain problems of a patient by stimulating muscles. The instant method is advantageous in muscle stimulation compared to other electrotherapeutic treatments in that fewer treatments are required with this process.

The afflictions and symptoms which can be treated are believed to be associated in some way with tissue damage including without limitation: inflammation; contusion; edema; hematoma; ulcers; block plasma kinins in particular bradykinins and affecting viral diseases and insect and snake bites; arthritis symptoms; strains; and sprains. The instant method can advantageously decrease pain associated with a traumatic injury.

The present method can be particulary useful in reducing inflammation. The process can be used to treat gingivitis; treat tendinitis including, but not limited to the achilles, elbow and hand; treat contusions including but not limited to the ankle, arm, breast, buttock, collarbone, elbow (to include the ulnar nerve), face, foot, hand, kidney, knee, leg, thigh, and wrist; treat synovitis including but not limited to the ankle, knee and hip; treat tenosynovitis including but not limited to the ankle, knee, hip, arm, shoulder, foot, hand and wrist, and treat shin splits. The treatment can be used to reduce or eliminate trauma induced edema. The present method can also reduce or eliminate hematoma including that of the foot, leg, thigh, arm, and hand. The treatment can also induce regeneration of soft tissue, bone and nerves.

The instant process can be used to: treat certain ulcers, especially gastrointestinal ulcers including particularly peptic and gastric; intervene in viral diseases and decrease or inhibit the increase of virus, possibly by increasing the efficacy of the immune system; stimulate hair growth and regrowth; and initiate cell dedifferentiation and the resulting redifferentiation by unlocking repressed genes.

The present process can be used to: block plasma kinins, in particular bradykinins, from receptor sites; neutralize inset and arachnid bits; neutralize poisonous snake bites, both protoplasmic and neurological; and anesthetize locally and globally. The instant process can be useful in the alleviation of drug dependency.

The treatment using the instant signal can also be used to maintain and increase the range of motion of body limbs. It can be useful in the treatment of strains, including, but not limited to, ankle, achilles tendon, abdominal wall, arm, back (grades 1 and 2, lumbodorsal region), back (grades 1 and 2, sacroiliac region), back (grades 1 and 2, lumbar region), chest muscle, collar bone, elbow, foot, groin, hand, hip, knee, leg, thigh, wrist, and fingers. Sprains can also be treated, including but not limited to, ankle, arm, back (grades 1 and 2, lumbodorsal region), back (grades 1 and 2, sacroiliac region), back (grades 1 and 2, lumbar region), breast bone (sternum), chest muscle, elbow, thumb and fingers. Relief of bursitis can also be provided, including, but not limited to that of the elbow, foot, hip and knee. Treatment of elbow epicondylitis (tennis elbow) can also be provided. Symptoms associated with arthritis can also be treated, including Reiter's syndrome. Tendonitis, including that of the achilles, elbow and hand can also be treated.

The application of the above-described signal is useful in stimulating muscles. Afflictions and symptoms associated with muscle spasms or weakness can be treated with the instant process.

The application of such a signal is useful in promoting the relaxation of muscle spasms, for example, the relaxation of muscle cramps, the treatment of menstrual cramps and the treatment of hiccups. The treatment can also be used to relieve asthma, relax bronchial muscles, relieve exercise induced bronchospasm, and relieve bronchial cavity congestion. Relief of headaches can be achieved including migraine, tension and muscular. Relief of vascular spasms can also be achieved. The treatment can also be used to relax intestinal muscle spasm including providing relief of diarrhea.

Prevention and retardation of disuse atrophy can also be accomplished, for example treatment of damage of the thigh hamstring. Similarly, the treatment can be used to correct muscle weakness, increase muscle strength and improve muscle tone.

The present process is also useful for muscle re-education, for example correction of muscle weakness, increasing muscle tone and increasing muscle stretch. Application of the periodic-exponential signal can be useful in correcting certain vision system defects by balancing the various muscles associated with the eyeball. The method can be used to treat scoliosis; reduce fatty tissue; and reduce pain, specifically but not limited to lower back pain. Cosmetic body alteration can be accomplished including but not limited to face lift, breast toning, buttock toning and lifting (tucking). The process can also be used to treat hernias (hiatal).

Application of the above-described signal can also be used to reduce stress. The instant process can also be used to provide immediate post-surgical stimulation of calf muscle to prevent venous thrombosis.

Local blood circulation can also be increased through use of the instant treatment. The increase in blood circulation can be beneficial in the treatment of (a) treatment of bone fractures to facilitate mending, (b) treatment of dislocations in any joints, (c) accelerated healing of damaged tissue, and (d) accelerated healing of spinal injuries.

In the treatment of a patient for muscle spasms, the muscle which is in spasm should be determined. Preferably, treatment is effected along the longitudinal axis of the muscle. Preferably a pad is placed at teach end of the muscle along the longitudinal axis of the muscle with the muscle itself between the pads. If the muscle being treated is a frontal muscle, then the pad should be placed on the frontal part of the body. If a dorsal or posterior muscle is involved, then the pads should be placed on the dorsal part of the body. If it is not possible to treat longitudinally, transverse treatment can be effective. In this case, the pads are placed perpendicular to the longitudinal axis of the muscle being treated. For example, if hiccups are being treated, transverse stimulation of the diaphragm is preferred. One pad can be placed anterior just below the sternum. The other pad can be placed on the body posterior substantially opposite to the first pad.

The same method of treatment is preferred for preventing a retarding disuse atrophy. Two pad pairs can be used simultaneously to provide more time-effective treatment.

To increase local blood circulation, the treatment region must be determined. If the region is in a limb, treatment is applied transversely be placing a pair of pads so that the region to be treated lies between them. For example, if a knee is being treated, one pad is placed on the inside of the knee while the other pad is placed on the outside of the knee. If the region to be treated is in the body, transverse treatment is similarly preferred, with one pad being placed on the front portion of the body and the other pad placed on the back part of the body. Once again, two pad pairs can be used for more efficient time utilization.

To re-educate muscles, the muscles or muscle groups to be treated should be determined. The same procedure is followed as in treating muscle spasms. Two pad pairs can be used. It is preferred to use continuous-on treatment for the desired period to maximize effect.

In the treatment of calf muscles to prevent venous thrombosis, transverse treatment is preferred. Both pads are preferably placed on the mid-calf with one pad on the inside of the leg and the other on the outside. Optionally, both legs can be treated simultaneously.

The treatment for maintaining an increase in the range of motion involves determining which joint and associated muscle groups are to be treated. Generally, the preferred treatment is transverse across the joint being treated. If the joint is the knee, ankle or elbow, one pad is placed on the inside of the joint with the other pad being place on the outside relative to the body. If edema is present, a first pad should be placed on the edema with the second pad diametrically opposed thereto. If the joint being treated is the shoulder, wrist, knuckle or finger joints, preferably one pad is placed on the front with the other pad placed on the back of the joint. The foot and toe joints are treated by placing one pad on the top of the joint with the other pad beneath the joint. In the treatment of a hip joint, a remote treatment technique is used. The pads are placed over the posterior ilium slightly above the gluteal maximum. When the region being treated is the back for limited body rotation, stiff neck, limited anterior-posterior bending motion, etch., the preferred treatment is longitudinal in the muscle groups running up and down the left and right sides of the spine. The exact pad placement is determined in a manner similar to that used for muscle spasms.

In the treatment of ulcers, specifically, but not limited to peptic and gastric, the preferred method of treatment is to place the pads transverse. After determining the location of the pain, one pad is placed over the point of pain on the anterior of the body and the other pad is placed on the posterior surface of the body. Preferably, neither pad is inferior (below) or superior (above) the other. Preferably a twenty minute treatment is used at maximum amplitude settings consistent with patient comfort.

The general treatment technique of viral caused diseases is by the transverse stimulation of the lymph node area in the neck and the spleen. Preferably, the pads are placed anterior and posterior to the organ being treated. However, if the throat is being treated, the pads can be placed in lateral positions on the left and right side of the throat. Normally, a twenty minute treatment is used at maximum amplitude setting consistent with patient comfort. The optimal treatment period is three consecutive days.

Certain vision system defects can be corrected by balancing the relative strength of various muscles associated with the eyeball. In the treatment, one pad pair is used for treatment of a single eye. It is preferred that only one eye be treated at a time. This treatment technique involves "indirect" stimulation to the intrinsic ciliary muscle since neither longitudinal nor transverse stimulation is possible. It is expected that miniaturized pads on LOW powers settings are required. The amplitude should be adjusted only to the very low edge of patient awareness. The treatment time should be limited to not more than five minutes. Total treatment time varies greatly from patient to patient depending on the nature of the condition and its severity.

In using the instant process to selectively block plasma kinins from its receptor sites, in particular bradykinin, any pad placement can be used. This effect occurs quickly with upper comfort range power settings. The effects appear to be long term in nature. This effect appears to be directly related to the reduction of inflammation and to the reduction of trauma induced edema.

The preferred means for applying the periodic-exponential signal to a patient and the proper placement of the application means on the patient can be readily determined. The proper placement of the application means for the treatment of other afflictions can be readily accomplished to effect the most efficient treatment. As discussed hereinabove, the initial placement will depend upon the location of the afflictions with transverse placement of the application means being initially tried.

With references to FIGS. 6A-D, a preferred embodiment of an apparatus for use in applying an electrical signal to a structure associated with the eye of a patient 170, hereinafter referred to as apparatus 170, is illustrated. The apparatus 170 includes first and second electrodes 172a, 172b, for conducting an electrical signal of which at least a portion is to be applied to a structure associated with a patient's eye. First and second electrodes 172a, 172b, are adapted for application to the exterior surface of a patient and are preferably made of a conductive, carbonized rubber material, such as the conducting carbonized rubber material sold by Amprex under the trademark FLEXTRODE. The first and second electrodes 172a, 172b, interface with the devices for generating electrical signals shown in FIGS. 1, 4, and 5 via first and second electrical leads 174a, 174b, and first and second connectors 176a, 176b.

The apparatus 170 further includes a positioning device 178 for positioning the first and second electrodes 172a, 172b, at a preferred point on the exterior surface of the patient for applying electrical signals to structures associated with the eye of the patient. More specifically, the positioning device 178 positions the first and second electrodes 172a, 172b, on the exterior surface of a patient at a location that is substantially interior to the area defined by the bones that form the frontal aspect of the eye socket, the Supraorbital Ridge and the Zygoma or Mazar bones. The positioning device 178 includes a base member 180 that supports first and second vertical members 182a, 182b. Supported by the first and second vertical members 182a, 182b, is a first cross member 184 for use in supporting the chin area of the patient. The first cross member 184 includes a first horizontal member 186 on the upper side of which is located a chin pad 188. The first horizontal member 186 includes first engaging members 190a, 190b, for contacting the first and second vertical members 182a, 182b. The first cross member 184 further includes first adjustment screws 192a, 192b, for fixing the first cross member 184 at a particular vertical position on the first and second vertical members 182a, 182b. The positioning device 178 also includes a second cross member 194 for use in supporting the forehead region of the patient. The second cross member 194 includes a second horizontal member 196 that is curved to conform to the forehead region of the typical patient. Attached to the side of the second horizontal member 196 against which the patient's forehead rests is a forehead pad 198. The second horizontal member 196 includes second engaging members 200a, 200b, for engaging the first and second vertical members 182a, 182b. Second adjustment screws 202a, 202b, are provided for adjusting the vertical position of the second cross member 194 on the first and second vertical members 182a, 182b.

The elements of the positioning device 178 described thus far serve to stabilize the patient's head during application of an electrical signal to a structure associated with the patient's eye. More specifically, the first cross member 184 and the second cross member 194 are vertically positioned on the first and second vertical members 182a, 182b, using the first adjustment screws 192a, 192b, and the second adjustment screws 202a, 202b, to accommodate the dimensional characteristics of the patient's head. Once adjusted, the patient places their chin and forehead against the chin pad 188 and the forehead pad 198, respectively. Consequently, the elements of the positioning device 178 described thus far stabilize the patient's head in substantially one position for application of an electrical signal to a structure associated with the patient's eye. One advantage of the elements of positioning device 178 described thus far is that the patient can quickly and easily remove their head from the positioning device 178 if something should go wrong in applying the electrical signal to a structure associated with the patient's eye, thus reducing any possible damage that may result from application of the electrical signal.

The positioning device 178 also includes an electrode positioning member 204 for positioning the first and second electrodes 172a, 172b, at a location on the exterior of the patient that is substantially interior to the area defined by the bone structure comprising the frontal aspect of a patient's eye socket. The electrode positioning member 204 includes a first clamp member 206 and first set screw 208 for attaching and adjusting the position of the electrode positioning member 204 with respect to the first vertical member 182a. The first clamp member 206 also includes a hole 210 for receiving one end of a z-shaped rod 212. The rotational position of the z-shaped rod 212 with respect to first clamp member 206 and the positioning device 178 can be adjusted using a second set screw 214 that engages the first clamp member 206. Attached to the second end of the z-shaped rod 212 is a second clamp member 216. A third set screw 218 allows the rotational position of the second clamp member 216 relative to the z-shaped rod 212 to be adjusted. Attached to the second clamp member 216 are first and second electrode mounting members 220a, 220b. A fourth set screw 222 allows the vertical spacing of the first and second electrode mounting members 220a, 220b, to be adjusted to accommodate the vertical spacing between the bones that define the frontal aspect of the eye socket. To insulate the first and second electrodes 172a, 172b, from the second clamp member 216, which is presently made of an electrically conductive material, the first and second electrode mounting members 220a, 220b are coated with an insulating material, such as insulating rubber or thermoplastic.

The electrode positioning member 204 positions the first and second electrodes 172a, 172b, relative to the bone structure that defines the patient's eye socket after the patient's head is stabilized against the chin paid 188 and forehead pad 198 of the first cross member 184 and second cross member 194, respectively. By use of the first set screw 208, the electrode positioning member 204 can be vertically positioned on the first vertical member 182a at the appropriate level to accommodate the vertical position of the patient's eye socket. Moreover, the rotational position of the electrode positioning member 204 with respect to the first vertical member 182 can also be established to accommodate the orientation of the patient's eye socket relative to the positioning device 178 using the first set screw 208. The rotational position of the z-shaped rod 212 relative to the first clamp member 206 and the positioning device 178 can also be established using the second set screw 214. This is typically used to move the first and second electrodes 172a, 172b, towards or away from the center of the patient's face. The rotational position of the second clamp member 216 relative to the z-shaped rod 212 and the positioning device 178 is established using the third set screw 218 to a team. This allows the first and second electrodes 172a, 172b, to be positioned to accommodate the angle of the patient's eye socket with respect to the centerline of the patient's face. The fourth set screw 222 allows the vertical spacing of the first and second electrodes 172a, 172b, to be adjusted to accommodate the vertical spacing between the upper portion of the patient's eye socket and the lower portion of the patient's eye socket. More specifically, the fourth set screw 222 allows the first and second electrodes 172a, 172b, to be positioned at a location substantially interior to the area defined by the frontal edges of the patient's eye socket, the Supraorbital Ridge bone 224 and the Zygoma or Mazar bone 226.

In operation, a patient's head is stabilized in substantially one position using the apparatus 170 by initially adjusting the vertical positions of the first cross member 184 and the second cross member 194 using the first adjustment screws 192a, 192b, and the second adjustment screws 202a, 202b, to accommodate the dimensional characteristics of the patient's head. Once the appropriate adjustments have been made the patient places their head such that their chin engages the chin pad 188 and their forehead engages the forehead pad 198. Having stabilized the position of the patient's head, the electrode positioning member 204 is then used to position the first and second electrodes 172a, 172b, substantially flush against the exterior of the patient in an area substantially interior to the bone structure that defines the frontal aspect of the patient's eye socket. More specifically, the first set screw 208, the second set screw 214, and the third set screw 218 are used to adjust the position of the first and second electrodes 172a, 172b, such that they are located in the aforementioned position. Once the first and second electrodes 172a, 172b, are positioned at the aforementioned location, the fourth set screw 222 is used to adjust the vertical spacing between the first and second electrode mounting members 220a, 220b, such that the vertical dimension of the patient's eye socket is accommodated.

A structure to accommodate the horizontal dimension of the patient's eye socket has not been found to be necessary as of this time, but a structure for adjusting this aspect of the first and second electrodes 172a, 172b, is, of course, feasible. Moreover, an adjustment for horizontally off-setting the position of the first and second electrodes 172a, 172b, with respect to one another is also feasible. Additionally, an adjustment structure for moving the first and second electrodes 172a, 172b, independently towards and away from the patient's face is also feasible.

Once the first and second electrodes 172a, 172b, have been appropriately positioned using the positioning device 178, an electrical signal can then be applied to the first and second electrodes 172a, 172b, that results in an electrical signal being applied to one or more structures associated with the eye. These structures include structures interior to the eyeball, such as the vitreous humor, as well as structures exterior to the eyeball, such as the muscles that rotate the eyeball. Preferably, the signal that is applied to the structure associated with the eye is the signal illustrated in FIGS. 2A through 2C and FIG. 3, and produced by the apparatuses shown in FIGS. 1, 4, and 5. Characteristic of the signal shown in FIGS. 2A–C and FIG. 3 is that the signal possesses a shape that is believed to result in an electrical charge being imparted to one or more structures associated with the eye. This can be seen in FIGS. 2A and 2B where a greater portion of the signal is below the zero volt line than is above the zero volt line. Stated another way, an integral of the signal over time would be a non-zero value. This is believed to result in the aforementioned electrical charge being imparted to one or more structures associated with the eye. In any event, the signal illustrated in FIGS. 2A-C and FIG. 3 is believed to be effective in treating various ailments or maladies that affect various structures associated with the eye. Electrical signals with shapes different from that shown in FIGS. 2A-C and FIG. 3 are also feasible. An example of such a signal is a signal that includes a sinusoidal component as well as a DC component. In addition, the signal preferably has a RMS power level between approximately 4.75 milliwatts and 28 milliwatts. Presently, application and electrical signal to the eye of a patient using the apparatus 170 is believed to be effective in treating the following afflictions or maladies associated with structures involving the eye: Presbyopia, muscle imbalance, cataracts, glaucoma, inflammation, headache, iritis, anterior ureitis, posterior ureitis, optic nerve neuritis, optic nerve ischemia, and visual field defects.

The foregoing description of the invention has been presented for purposes of illustration and description. Further, the description is not intended to limit the invention to the form disclosed therein. Consequently, variations and modifications commensurate with the above teachings, and the skill or knowledge in the relevant art are within the scope of the present invention. The preferred embodiment described hereinabove is further intended to explain the best mode known of practicing the invention and to enable others skilled in the art to utilize the invention in various embodiments and with the various modifications required by their particular applications or uses of the invention. It is intended that the appended claims be construed to include alternative embodiments to the extent permitted by the prior art.

What is claimed is:

1. An apparatus for use in non-invasively applying an electrical signal to a structure associated with the eye of a patient, comprising:
    means for conducting the electrical signal that includes a first electrode which is separated from a second electrode by a distance, wherein said first electrode and said second electrode are each adapted for application to the exterior surface of the patient; and
    means for use in positioning said first electrode and said second electrode on the exterior of the patient so that both said first electrode and said second electrode are at locations substantially interior to the same bone structure that defines one of the patient's eye sockets and includes means for adjusting said distance between said first electrode and said second electrode, wherein a substantial portion of the electrical signal is applied to a structure associated with the eye of the patient.

2. An apparatus, as claimed in claim 1, wherein:
    at least one of said first electrode and said second electrode has a first terminal end and a second terminal end, and an arcuate shape between said first terminal end and said second terminal end.

3. An apparatus for use in applying an electrical signal to a structure associated with the eye of a patient, comprising:
    means for conducting the electrical signal, wherein said means for conducting is adapted for application to the exterior surface of the patient; and
    means for positioning said means for conducting on the exterior of the patient, wherein a substantial portion of the electrical signal is applied to a structure associated with the eye of the patient, wherein said means for positioning includes means for substantially stabilizing the location of the head of the patient.

4. An apparatus, as claimed in claim 3, wherein:
    said means for positioning includes means for adjusting the position of said means for conducting to accommodate the orientation of the eye socket of the patient.

5. An apparatus for use in non-invasively applying an electrical signal to a structure associated with the eye of a patient, comprising:
    means for generating an electrical signal;
    means for conducting the electrical signal that includes a first electrode which is separated from a second electrode by a distance, wherein said first electrode and said second electrode are each adapted for application to the exterior surface of the patient; and
    means for use in positioning said means for conducting on the exterior surface of the patient so that both said first electrode and said second electrode are at locations that are substantially interior to the same bone structure that defines one of the patient's eye sockets, wherein said means for positioning includes means for adjusting said distance between said first electrode and said second electrode, wherein a substantial portion of the electrical signal is applied to a structure associated with the eye of the patient.

6. An apparatus, as claimed in claim 5, wherein:
    said electrical signal has an AC component.

7. An apparatus, as claimed in claim 5, wherein:
    said electrical signal includes an AC component and a DC component.

8. An apparatus, as claimed in claim 5, wherein:
    said electrical signal imparts an electrical charge to the structure associated with the eye of the patient.

9. An apparatus, as claimed in claim 5, wherein:
    said electrical signal has a sinusoidal component.

10. A method for non-invasively applying an electrical signal to a structure associated with the eye of a patient, comprising:
    generating an electrical signal;
    providing said electrical signal to a first electrode and a second electrode that is separated from said first electrode by a distance;
    adjusting said distance between said first electrode and said second electrode; and
    applying said first electrode and said second electrode to the exterior surface of the patient, wherein said first electrode and said second electrode are both located substantially interior to the same bone structure that defines one of the patient's eye sockets.

11. A method, as claimed in claim 10, wherein:
    said electrical signal improves at least one of the following: the strength, the flexibility, and the facility of a muscle structure associated with the eye.

12. A method, as claimed in claim 10, wherein:
    said electrical signal aids in the correction of one of the following afflictions: presbyopia, muscle imbalance, cataract, glaucoma, inflammation, headache, iritis, anterior uveitis, posterior uveitis, optic nerve neuritis, optic nerve ischemia, and visual field defects.

13. A method, as claimed in claim 10, wherein:
said electrical signal includes an AC component.

14. A method, as claimed in claim 10, wherein:
said electrical signal includes an AC component and a DC component.

15. An method, as claimed in claim 10, wherein:
said electrical signal imparts a charge to the structure associated with the eye.

16. A method, as claimed in claim 10, wherein:
said electrical signal includes a sinusoidal component.

17. A method for non-invasively applying an electrical signal to a structure associated with the eye of a patient, comprising:
stabilizing the position of the patient's head;
applying an electrical conductor to the exterior surface of the patient at a location substantially interior to the bone structure that defines the frontal aspect of the patient's eye socket;
generating an electrical signal; and
causing said electrical signal to be conducted by said electrical conductor;
wherein, said electrical signal is shaped to impart a charge to a structure associated with the patient's eye.

* * * * *